United States Patent
Khire et al.

(10) Patent No.: US 8,153,785 B2
(45) Date of Patent: Apr. 10, 2012

(54) STABILIZING LIGANDS FOR REGULATION OF PROTEIN FUNCTION

(75) Inventors: Uday Khire, Orange, CT (US); Davoud Asgari, Wilmington, NC (US)

(73) Assignee: Cheminpharma LLC, Farmington, CT (US)

( * ) Notice: Subject to any disclaimer, the term of this patent is extended or adjusted under 35 U.S.C. 154(b) by 214 days.

(21) Appl. No.: 12/754,707

(22) Filed: Apr. 6, 2010

(65) Prior Publication Data

US 2010/0267950 A1 Oct. 21, 2010

Related U.S. Application Data

(60) Provisional application No. 61/212,808, filed on Apr. 6, 2009.

(51) Int. Cl.
*C07D 413/12* (2006.01)
(52) U.S. Cl. ....................................... 544/130
(58) Field of Classification Search .................. 544/130
See application file for complete search history.

(56) References Cited

U.S. PATENT DOCUMENTS

| | | |
|---|---|---|
| 2009/0060888 A1 | 3/2009 | Crabtree et al. |
| 2009/0215169 A1 | 8/2009 | Wandless et al. |
| 2010/0034777 A1 | 2/2010 | Wandless et al. |

OTHER PUBLICATIONS

Schreiber, S. L., "The Small-Molecule Approach to Biology", Chem. Eng. News, vol. 81, No. 9, pp. 51-61 (2003).
Banaszynski, L. A. et al., "A Rapid, Reversable, and Tunable Method to Regulate Protein Function in Living Cells Using Synthetic Small Molecules", Cell, vol. 126, pp. 995-1004 (2006).
Holt, D. A. et al., "Recruitment of proteins to modulate protein-protein interactions", J. Am. Chem. Soc., vol. 115, pp. 9925-9938 (1993).
Yang, W. et al., "Investigating Protein-Ligand Interactions with a Mutant FKBP Possessing a Designed Specificity Pocket", J. Med. Chem., vol. 43, No. 6, pp. 1135-1142 (2000).
Grimley, J.S. et al., "Synthesis and analysis of stabilizing ligands for FKBP-derived destabilizing domains", Bioorg. Med. Chem. Lett., vol. 18, pp. 759-761 (2008).
Banaszynski, L. A. et al., "Chemical control of protein stability and function in living mice", Nat. Med., vol. 14, No. 10, pp. 1123-1127 (2008).
Clackson, T., "A Stability Switch for Proteins", Chem. Biol., vol. 13, pp. 926-928 (2006).
Lampson, M.A. et al., "Targeting Protein Stability with a Small Molecule", Cell, vol. 126, No. 5, pp. 827-829 (2006).
Kwan, M.D. et al., "Tunable control of FGF-2 secretion fro skeletal tissue engineering", J. Am. Coll. Surg., vol. 207 No. 3, supplement 1, pp. S63-S64 ( 2008).
Maynard-Smith, L. A. et al., "A Directed Approach for Engineering Conditional Protein Stability Using Biologically Silent Small Molecules", J. Biol. Chem., vol. 282, No. 34, pp. 24866-24872 (2007).
Hauske, J. R. et al., "Design and synthesis of novel FKBP inhibitors", J. Med. Chem., vol. 35, No. 23, pp. 4284-4296 (1992).
Kemsley, J., "Nobel Laureate Signature Award For Graduate Education in Chemistry", Chem. Eng. News, Jan. 26, p. 45 (2009).
Besong, G. et al., "Synthesis of (S)-(-)-N-acetylcolchinol using intramolecular biaryl oxidative coupling", Org. and Biomol. Chem., vol. 4, pp. 2193-2207 (2006).
Chu, G. W. et al., "Recent progress with FKBP-derived destabilizing domains", Biorg. Med. Chem. Lett., vol. 18, pp. 5941-5944 (2008).
Ryding, A.D.S. et al, "Conditional transgenic technologies", J. Endrocrinology, vol. 171, pp. 1-14 (2001).
Kuhn, R., et al., "Inducible gene targeting in mice", Science, vol. 269, No. 5229, pp. 1427-1429 (1995).
Vilella-Bach, M., et al., "The FKBP12-Rapamycin-binding Domain Is Required for FKBP12-Rapamycin-associated Protein Kinase Activity and G1 Progression", J. Biol. Chem., vol. 274. No. 7, pp. 4266-4272 (1999).
De Wolf, F. et al., "Ligand-Binding Proteins: Their Potential for Application in Systems for Controlled Delivery and Uptake of Ligands", Pharmacol. Rev., vol. 52, No. 2, pp. 207-236 (2000).
Sellmyer, M.A., et al., "A General Method for Conditional Regulation of Protein Stability in Living Animals", Cold Spring Harb. Protoc., vol. 2009, No. 3, doi:10.1101/pdb.prot5173 (2009).
Hagan, E. L., et al., "Regulating Protein Stability in Mammalian Cells Using Small Molecules", Cold Spring Harb. Protoc., vol. 2009, No. 3, doi:10.1101/pdb.prot5172 (2009).

*Primary Examiner* — Rebecca Anderson
(74) *Attorney, Agent, or Firm* — David W. Ladner; Ladner Patent Management LLC

(57) ABSTRACT

The invention pertains to novel compounds of Formula (I) wherein $R^1$, $R^2$, $R^3$, W, Y, Z, A, m, n, p, and q are defined herein. Such compounds are useful as stabilizing ligands in systems that assist in the determination of protein function.

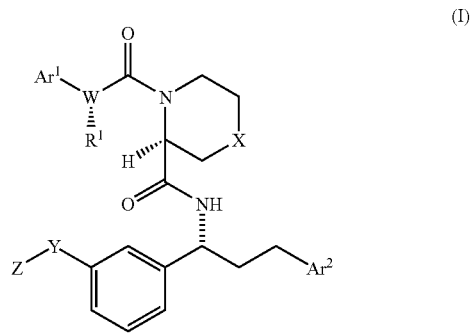

3 Claims, No Drawings

STABILIZING LIGANDS FOR REGULATION OF PROTEIN FUNCTION

RELATED APPLICATION

This patent application claims priority to U.S. Provisional Patent Application Ser. No. 61/212,008, filed Apr. 6, 2009, the content of which is incorporated herein by reference in its entirety.

FIELD OF THE INVENTION

Provided are novel ligand molecules which bind to specific protein sequences that, in the absence of ligand, impart instability to the entire protein into which it is inserted. Such ligands and ligand/protein systems are useful for determining protein function. Also provided are methods for preparation of the stabilizing ligands.

BACKGROUND OF THE INVENTION

Medical therapies frequently depend on the ability to control the function of specific proteins in vivo, thereby altering the disease state. For example, various recombinant genetic treatments have been used to supplement or replace proteins which are absent or insufficiently produced due to disease. Conversely, many drug therapies rely on the inhibition of protein function which is elevated in the disease state, and their discovery can depend on measurement of the effectiveness of a drug candidate's inhibition. Specifically, in vitro and in vivo assays (Cell based or animal models) are routinely developed to identify new drug candidates, and optimize structures based on inhibitory data. These assays are relied upon for predicting the effectiveness of drug treatments while minimizing unwanted interactions with non-target proteins.

The discovery of protein-based targets in an organism and the effect of regulation of this target on a disease state has become a well-accepted method for identifying molecules that affect them; see for example, S. L. Schreiber, *Chem. Eng. News.* 2003, 81(9), 51-61. These molecules provide leads to new drug classes and eventually to useful pharmaceuticals substances.

Many protein targets are now known or implicated in medical research and often routinely used in drug discovery research. However, it is expected that many more remain to be discovered and understood. Several methods have been described which are used in this discovery effort, such those described in L. A. Banaszynski et al., *Nat. Med.,* 2008, 14 (10), 1123-1127, and references therein. These include the use of hosts in which specific genes have been silenced, i.e., knockouts, and observation of the resulting effect in vivo. Also known is the so called Cre-loxP system (A. D. S. Ryding et al., *J. Endrocrinol.,* 2001, 171, 1-14 and R. Kuhn et al., *Science,* 1995, 269, 1427-1429.) In the 2008 Banasynski 2008 reference there is reported a general system useful for studying the function of specific proteins in a more directed and precise manner. A gene sequence coded for the protein of interest and as well as a small, destabilizing protein (known as FKBP L106P) is engineered and inserted in to a cell line of interest. The fused protein, although expressed, becomes destabilized, but is rescued by addition of a stabilizing ligand which binds to the destabilizing FKBP L106 domain. The amount of protein available can thus be controlled by the amount of stabilizing ligand added to the cell or organism in which the protein is expressed. The ability to effect stabilization has been also demonstrated in cultured cells. (Banaszynski et al., 2006). The applicability of the technique to living organisms was demonstrated by the successful introduction of a cytokine IL-2/FKBP L106P sequence into the HCT116 cancer cell line, and the formed tumor was introduced by xenograph into mice. The amount of IL-2 in the animal was dependent on the amount of stabilizing ligand (designated as Shield-1) introduced into the mouse. Demonstrating the ability to control IL-2 (Interleukin-2) is significant because it is a protein useful in recombinant gene therapies for treating cancer.

Stabilizing ligands, (Shield-1 and Shield 2) and their binding behavior to the FKBP L106P destabilizing domain, are specifically described by J. S. Grimley et al., *Bioorg. Med. Chem. Lett.,* 2008, 18, 759-761.

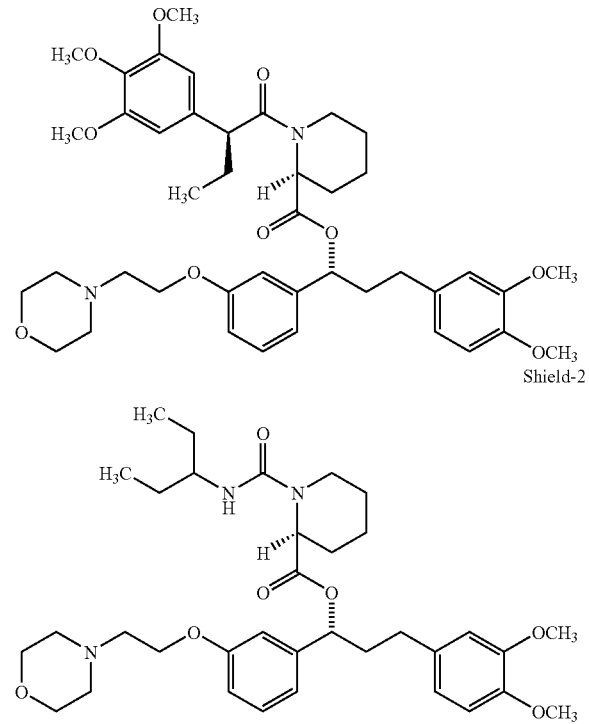

To broaden the applicability of this research tool, stabilizing ligands other than Shield-1 or Shield-2, that do not materially diminish the binding affinity to the FKBP L106P destabilizing domain, but have advantageous physicochemical properties would be useful. Because of the variety of physiological conditions under which proteins may exist in vivo (variable pH, exposure to proteases and other metabolizing enzymes), ligands with improved exposure characteristics, i.e., pharmacological properties would be useful. Such characteristics would be, for example, improved aqueous solubility and greater chemical stability, i.e., resistance to hydrolysis or digestion. These ligands may lead to a more convenient route of administration such as intra-venous or oral. In addition, ligands that are readily accessible by straightforward synthetic methods would be desirable.

REFERENCES

S. L. Schreiber, *Chem. Eng. News.* 2003, 81(9), 51-61
L. A. Banaszynsi et al., *Cell* 2006, 126, 995-1004.
D. A. Holt et al., *J. Am. Chem. Soc.,* 1993, 115, 9925-9938.
W. Yang et al., *J. Med. Chem.,* 2000, 43(6), 1135-1142.
J. S. Grimley et al., *Bioorg. Med. Chem. Lett.,* 2008, 18, 759-761.
L. A. Banaszynski et al., *Nat. Med.,* 2008, 14 (10), 1123-1127.
T. Clackson, *Chem. Biol.,* 2006, 13, 926-928.
M. A. Lampson et al., *Cell,* 2006, 126 827-829.

M. D. Kwan et al., *J. Am. Coll. Surg.*, 2008, 207 (3, supplement 1), S63-S64.
L. A. Maynard-Smith et al., *J. Biol. Chem.*, 2007, 282 (34), 24866-24872.
J. Kemsley, *Chem. Eng. News,* 2009, January 26, 45.
G. W. Chu et al., *Biorg. Med. Chem. Lett.,* 2008, 18,5941-5944.
J. R. Hauske et al., *J. Med. Chem.*, 1992 35 (23), 4284-4296.
G. Besong et al., *Org. and Biomol. Chem.*, 2006, 4, 2193-2207.
T. J. Wandless et al., US Patent Application 2009/0215169
T. J. Wandless et al., US Patent Application 2010/0034777
G. R. Crabtree et al., US Patent Application 2009/0060888

DETAILED DESCRIPTION OF THE INVENTION

The invention pertains to compounds of Formula (I)

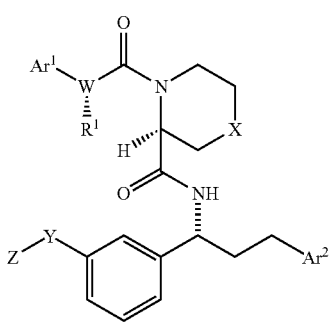

(I)

wherein
W is CH or N;
$R^1$ is $(C_1$-$C_6)$alkyl;
Y is O, $CH_2$, S, NH, or $NR^2$;
$R^2$ is $(C_1$-$C_6)$alkyl;
X is $CH_2$, O, NH, N$((C_1$-$C_6)$alkyl);
Z is selected from

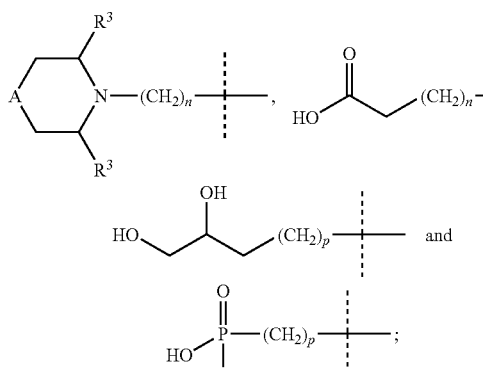

wherein
A is O, $CH_2$, S, NH, or $NR^2$;
$R^3$ is $(C_1$-$C_6)$alkyl;
n is 1, 2, 3, 4 or 5;
p is 0, 1, 2, 3, 4 or 5;
$Ar^1$ and $Ar^2$ are each independently phenyl, optionally substituted by 1-3 groups selected from $(C_1$-$C_3)$alkyl, $(C_1$-$C_3)$alkoxy, and halo;
and the pharmaceutically acceptable salts thereof.

Such compounds are useful as stabilizing ligands in systems that assist in the determination of protein function.

An embodiment of the invention is the compound of Formula (Ia)

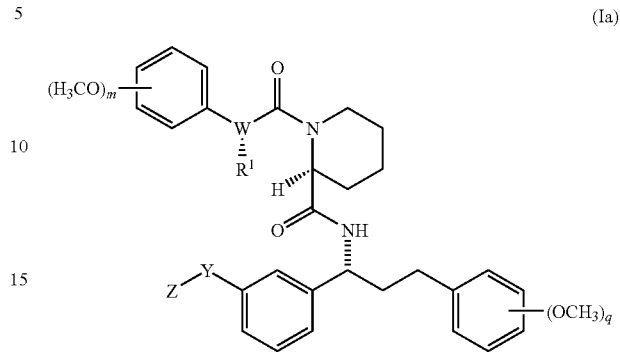

(Ia)

wherein
W is C or N;
$R^1$ is $(C_1$-$C_6)$alkyl;
Y is O, $CH_2$, S, NH, or $NR^2$;
m is 0, 1, 2 or 3;
q is 0, 1 or 2;
Z is

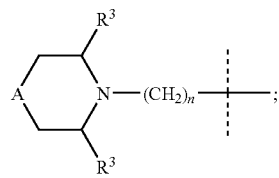

wherein
n is 2, 3, 4 or 5;
A is O, $CH_2$, S, NH, or $NR^2$;
$R^2$ and $R^3$ are independently $(C_1$-$C_6)$alkyl;
and the pharmaceutically acceptable salts thereof.

Another embodiment of the invention is the compound of Formula (Ic)

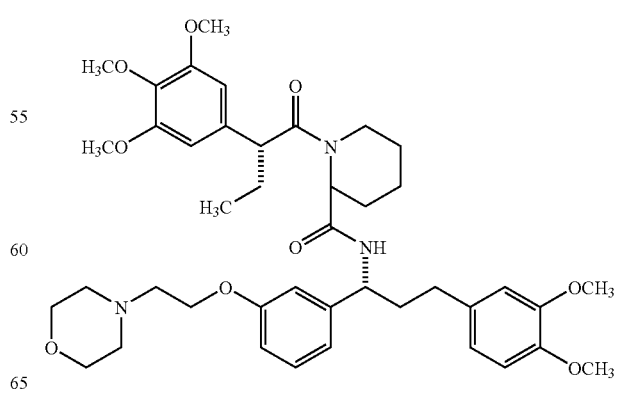

(Ic)

Yet another embodiment of the invention is the compound of Formula (Id):

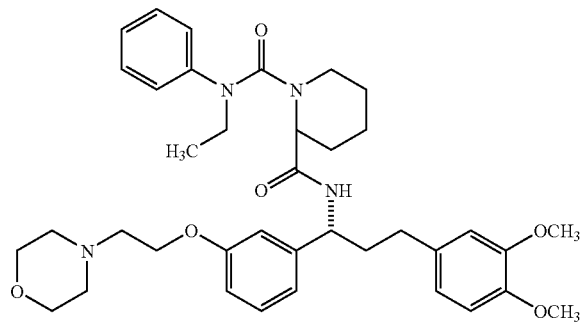

Also provided is a method of preparation of the compound of Formula (I) comprising the coupling of compounds of general formula 1 and general formula 2, as illustrated below in Scheme 1.

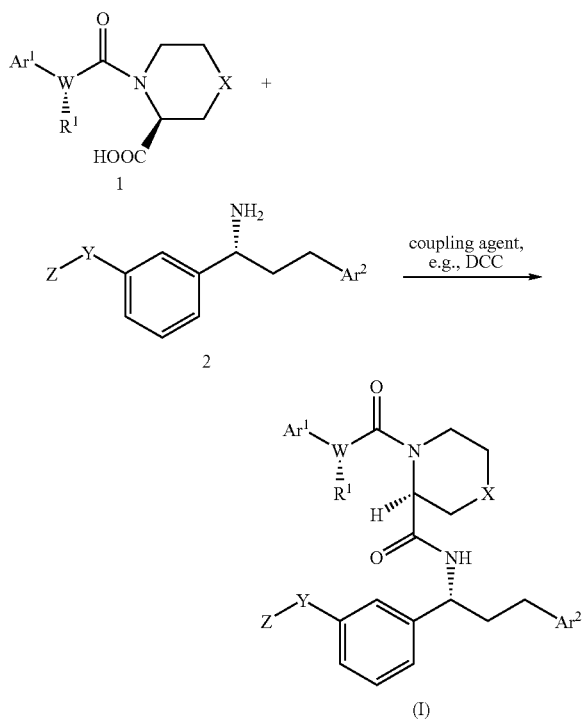

DEFINITIONS

The terms identified above have the following meaning throughout:

The term "optionally substituted" means that the moiety so modified may have from none to up to at least the highest number of substituents possible. The substituent may replace any H atom on the moiety so modified as long as the replacement is chemically possible and chemically stable. When there are two or more substituents on any moiety, each substituent is chosen independently of any other substituent and can, accordingly, be the same or different.

The term "halo" means an atom selected from Cl, Br, F, and I.

The terms "$(C_1-C_3)$alkyl" and "$(C_1-C_6)$alkyl" mean linear or branched saturated carbon groups having from about 1 to about 3, or from about 1 to about 6 C atoms, respectively. Such groups include, but are not limited to, methyl, ethyl, n-propyl, isopropyl, pentyl, hexyl and the like.

The terms "$(C_1-C_3)$alkoxy" and "$(C_1-C_6)$alkoxy" mean a linear or branched saturated carbon group having from about 1 to about 3, or from about 1 to about 6 C atoms, respectively, said carbon group being attached to an oxygen atom. The oxygen atom is the point of attachment of the alkoxy substituent to the rest of the molecule. Such groups include, but are not limited to, methoxy, ethoxy, n-propoxy, isopropoxy, and the like.

When a phenyl ring is substituted with one or more substituents, the substituent(s) may be attached to the phenyl ring at any available C atom. When there is more than one substituent on a phenyl ring, each substituent is selected independently from the other so that they may be the same or different.

A salt of a compound of Formula (I) may be prepared in situ during the final isolation and purification of a compound or by separately reacting the purified compound in its free base form with a suitable organic or inorganic acid and isolating the salt thus formed. Likewise, when the compound of Formula (I) contains a carboxylic acid moiety, a salt of said compound of Formula (I) may be prepared by separately reacting it with a suitable inorganic or organic base and isolating the salt thus formed The term "pharmaceutically acceptable salt" refers to a relatively non-toxic, inorganic or organic acid addition salt of a compound of the present invention (see, e.g., Berge et al., J. Pharm. Sci. 66:I-19, 1977).

Representative salts of the compounds of Formula (I) include the conventional non-toxic salts and the quaternary ammonium salts which are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, tartrate, thiocyanate, tosylate, undecanoate, and the like.

Base salts include, for example, alkali metal salts such as potassium and sodium salts, alkaline earth metal salts such as calcium and magnesium salts, and ammonium salts with organic bases such as dicyclohexylamine and N-methyl-D-glucamine. Additionally, basic nitrogen containing groups in the conjugate base may be quaternized with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides; aralkyl halides like benzyl and phenethyl bromides, and the like. When a phenyl ring is substituted with one or more substituents, the substituent(s) may be attached to the phenyl ring at any available C atom. When there is more than one substituent on a phenyl ring, each substituent is selected independently from the other so that they may be the same or different.

Preparation of Compounds of the Inventions

The particular process to be utilized in the preparation of the compounds of this invention depends upon the specific compound desired. Such factors as the specific substituents possible at various locations on the molecule, all play a role in the path to be followed in the preparation of the specific compounds of this invention. Those factors are readily recognized by one of ordinary skill in the art.

Compounds of the present invention may be made according to the following Reaction Schemes 1-5. In these schemes, unless otherwise noted, $R^1$, $R^2$, $R^3$, W, Y, Z, A, m, n, p, and q have the same definitions as described above.

Reaction Scheme 2 illustrates a general method of preparation of compounds of Formula (I).

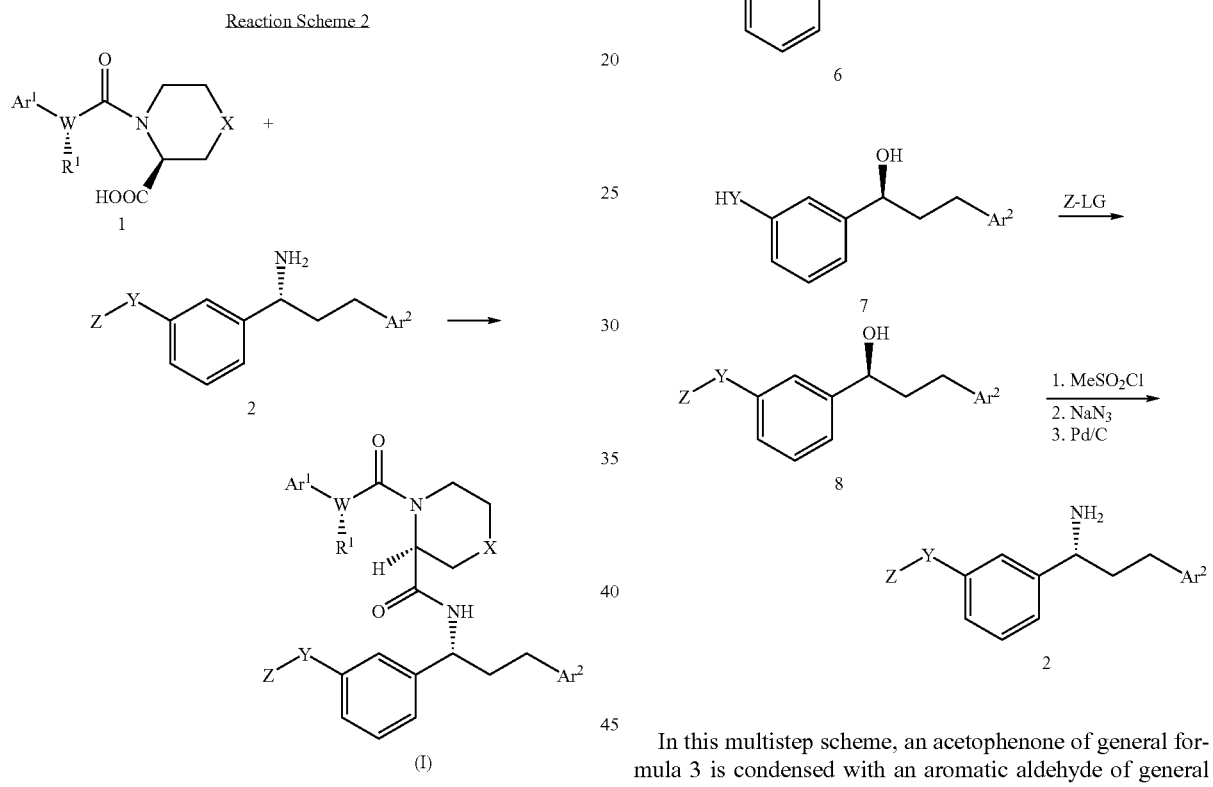

In this scheme, the cyclic amino acid of general formula 1 is coupled with an amine of general formula 2 to form the product of Formula (I). To aid in this coupling, a dehydrating agent catalyst may be used such as dicyclohexylcarbodiimide (DCC).

The intermediate amine of general formula 2 is prepared as shown in Reaction Scheme 3.

Reaction Scheme 3

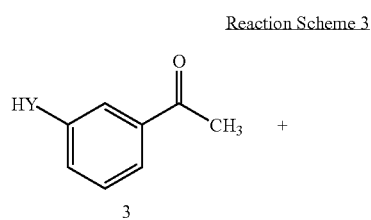

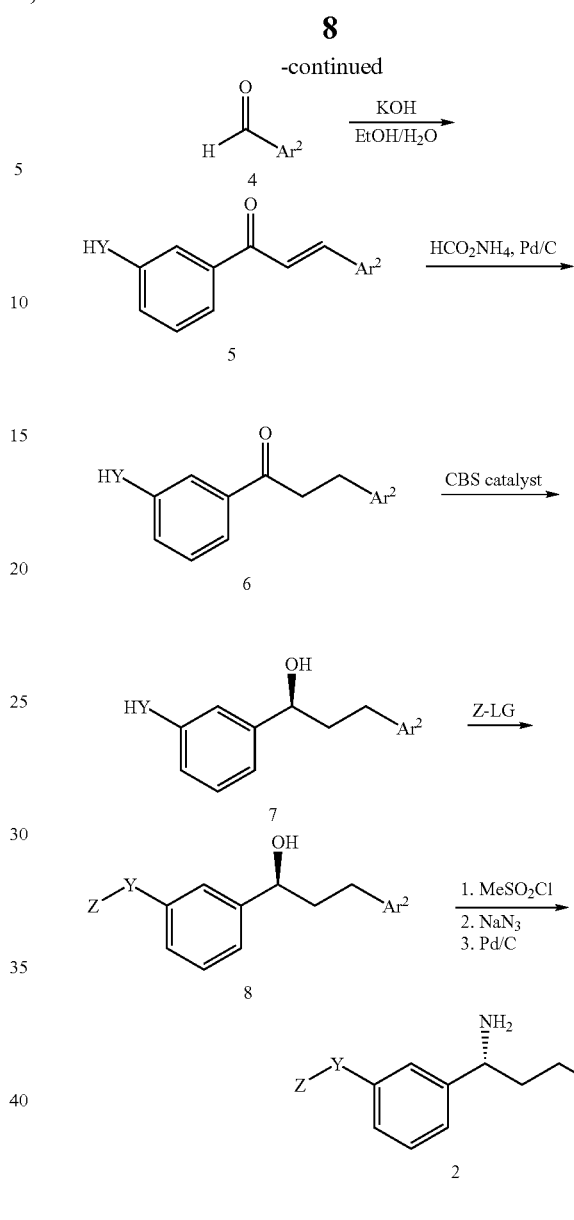

In this multistep scheme, an acetophenone of general formula 3 is condensed with an aromatic aldehyde of general formula 4 under basic conditions to provide the enone of general formula 5. Reduction of the double bond, using, for example ammonium formate and a palladium catalyst, provides the ketone of general formula 6. Chiral reduction of the ketone 6 with CBS catalyst (Besong et al., 2006) provides the chiral alcohol of general formula 7. Alkylation of the YH moiety on the formula 7 compound with reagents of general formula Z-LG, where Z is as defined above and LG is a suitable leaving group such as halo or methanesulfonate, leads to the compound of general formula 8. The chiral alcohol is then converted to the chiral amine in a sequence which results in inversion of configuration, for example, conversion of the alcohol to a methanesulfonate, displacement with sodium azide and reduction of the azide with Pd/C under a hydrogen atmosphere.

The amino acid of general formula 1a (general formula 1 where W is CH), used in the preparation of Formula (I) compounds where W is CH, is prepared as shown in Reaction Scheme 4.

Reaction Scheme 4

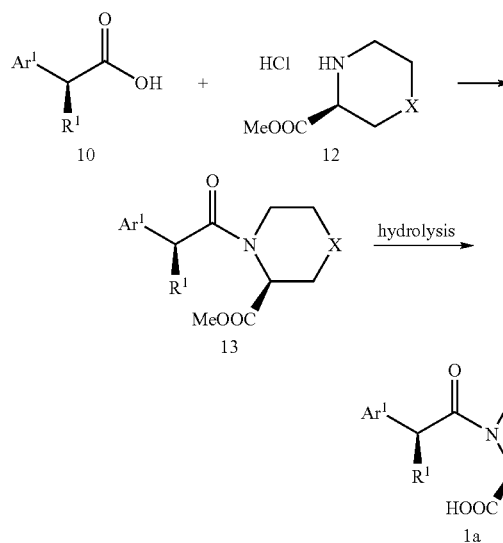

In this scheme, a chiral carboxylic acid of general formula 10 is coupled with a cyclic amino ester of general formula 12, using a coupling agent such as 2-chloro-1-methyl-pyridinium iodide, to give the ester amide of general formula 13. Hydroysis of the ester gives the acid amide of general formula 1a.

The amino acid of general formula 1b (general formula 1 where W is N), used in the preparation of formula (I) compounds where W is N, is prepared as shown in Reaction Scheme 5.

Reaction Scheme 5

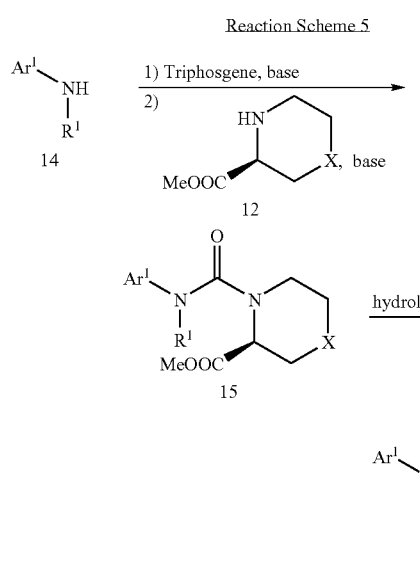

In this scheme, a substituted aromatic amine of general formula 14 and the cyclic amino ester of general formula 12 are linked using triphosgene to form an ester urea of general formula 15, and subsequently hydrolyzed to the acid urea of formula 1b.

The compound of general formula 12, used in the preparation of compounds of general formula 1a and 1b is prepared by esterification of the cyclic amino acid as shown in Reaction Scheme 6.

Reaction Scheme 6

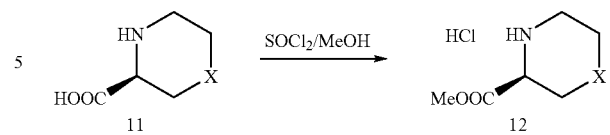

The carboxylic acid intermediate of general formula 10 is prepared by alkylation of the carboxylic acid of general formula 15, followed by chiral resolution in a manner described in the art (Holt D. A, 1993) as illustrated in Reaction Scheme 7.

Reaction Scheme 7

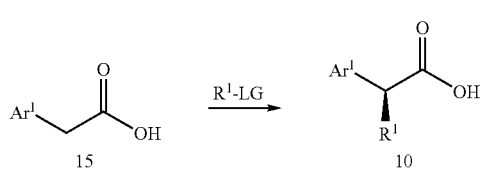

Sensitive or reactive groups on any of the intermediate compounds may need to be protected and deprotected during any of the above methods for forming esters. Protecting groups in general may be added and removed by conventional methods well known in the art (see, e.g., T. W. Greene and P. G. M. Wuts, Protective Groups in Organic Synthesis; 4th edition Wiley: New York, 2006).

Method of Using Compounds of Formula (I)

Compounds of Formula (I) can be used in the manner analogous described for Shield-1, in L. A. Banaszynski et al., 2006, Cell, 126, 995-1004, and references therein. It is to be understood that the compounds may be dissolved in one or more suitable solvents, formulated with inert carriers, or with diluents or excipients to facilitate administration and control precise dosing.

General Experimental Methods

In general, the compounds used in this invention may be prepared by standard techniques known in the art, by known processes analogous thereto, and/or by the processes described herein, using starting materials which are either commercially available or producible according to routine, conventional chemical methods. The following preparative methods are presented to aid the reader in the synthesis of the compounds of the present invention.

Air and moisture sensitive liquids and solutions were transferred via syringe or cannula, and introduced into reaction vessels through rubber septa. Commercial grade reagents and solvents were used without further purification. The term "concentration under reduced pressure" or "in vacuo" refers to use of a Buchi rotary evaporator at approximately 15 mm of Hg. All temperatures are reported uncorrected in degrees Celsius (° C.).

Thin layer chromatography (TLC) was performed on EM Science pre-coated glass-packed silica gel 60 A F-254 250 pm plates. Column chromatography (flash chromatography) was performed on a Combiflash system using 32-63 micron, 60 Å, silica gel pre-packed cartridges. Purification using preparative reversed-phase HPLC chromatography was accomplished using a Gilson 215 system, using a YMC Pro-C18 AS-342 (150×20 mm I.D.) column. Typically, the mobile phase used was a mixture of H$_2$0 (A) and MeCN (B). The water may be mixed with 0.1% TFA. A typical gradient is described below:

HPLC method (method H): Phenomenex C18 (150×30 mm) 5μ column, 5% acetonitrile to 90% acetonitrile over 20 min, flow 20 mL/min LC-MS/MS Method: Zorbax C18 (15 cm×2.1 mm) column, Solvent A: acetonitrile with 0.1% formic acid, Solvent B: water with 0.1% formic acid, gradient 5% A to 85% A over 15 min.

Routine one-dimensional NMR spectroscopy was performed on 400 or 500 MHz Varian Mercury-plus spectrometers. The samples were dissolved in deuterated solvents obtained from Cambridge Isotope Labs, and transferred to 5 mm ID Wilmad NMR tubes. The spectra were acquired at 293° K. The chemical shifts were recorded on the ppm scale and were referenced to the appropriate residual solvent signals, such as 2.49 ppm for DMSO-d$_6$, 1.9 3 ppm for CD$_3$CN, 3.30 ppm for CD$_3$OD, 5.32 ppm for CD$_2$Cl$_2$, and 7.26 ppm for CDCl$_3$ for $^1$H spectra, and 39.5 ppm for DMSO-d$_6$, 1.3 ppm for CD$_3$CN, 49.0 ppm for CD$_3$OD, 53.8 ppm for CD$_2$Cl$_2$, and 77.0 ppm for CDCl$_3$ for $^{13}$C spectra.

General methods of preparation are illustrated in the reaction schemes, and by the specific preparative examples that follow.

Abbreviations and Acronyms

When the following abbreviations are used herein, they have the following meaning:
anhy anhydrous
Bu butyl
n-BuOH n-butanol
t-BuOH tert-butanol
t-BuOK potassium-tert-butoxide
CBS Corey-Bakshi-Shibata catalyst
CD$_3$OD methanol-d$_4$
CI-MS chemical ionization mass spectrometry
conc concentrated
DCC dicyclohexylcarbodiimide
DCM dichloromethane
DMAP 4-dimethylaminopyridine
DMF N,N-dimethylformamide
DMSO dimethyl sulfoxide
ee enantiomeric excess
EI-MS electron impact mass spectrometry
ES-MS electrospray mass spectrometry
Et$_3$N triethylamine
EtOAc ethyl acetate
EtOH ethanol
Et$_2$O ethyl ether
GC-MS gas chromatography-mass spectrometry
h hour
HPLC high performance liquid chromatography
IL-2 interleukin-2 protein
LC-MS liquid chromatography-mass spectrometry
LG leaving group
Me methyl
MeOH methanol
mg milligram
mL milliliter
mmol millimole
NMR nuclear magnetic resonance
ppm part per million
Rf retention factor
RT retention time
rt room temperature
THF tetrahydrofuran
TFA trifluoroacetic acid
TLC thin layer chromatography
UV ultraviolet

EXPERIMENTAL EXAMPLES

Example 1

Preparation of 3-((S)-1-hydroxy-3-(3,4-dimethoxyphenyl)phenol

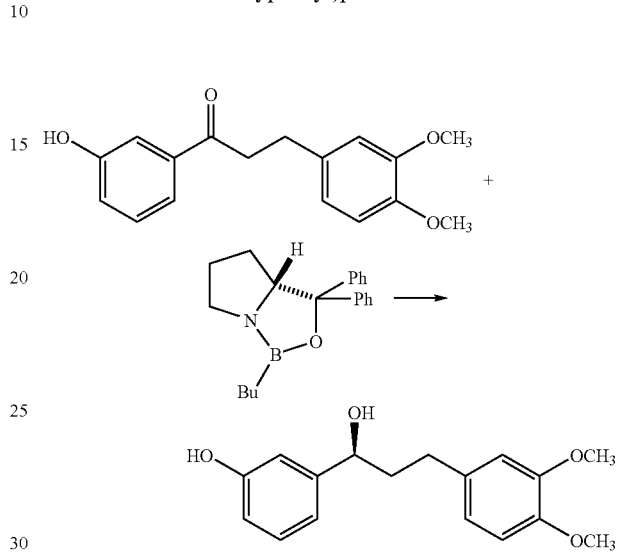

1-(3-Hydroxyphenyl)-3-(3,4-dimethoxyphenyl)propan-1-one (1.0 g, 3.5 mmol, prepared as described in the procedure of Holt et al., 1993) was dissolved in anhy THF (10.0 mL). In a separate flask, BH$_3$.SMe$_2$ (0.18 mL, 0.35 mmol) was added to a solution of 0.2 M of (S)-(−)-2-(diphenylhydroxymethyl) proline (CBS, 0.35 mmol, 1.8 mL, prepared as described by E. J. Corey et al., 1988, *J. Org. Chem.*, 53, 2861-2863) in toluene. To this solution were simultaneously added the ketone solution in THF and BH$_3$.SMe$_2$ (3.2 mL, 5.9 mmol) within 1 h period. The reaction mixture was stirred at rt for 45 min, then 1 mL MeOH was added drop by drop, followed by 3 mL of 1 N HCl, and the mixture was extracted with DCM. The organic layer was washed with water, brine and the combined extracts were dried over anhy MgSO$_4$. Evaporation of the solvent afforded the product as yellow oil (1.0 g, quantitative yield).

$^1$H NMR (500 MHz, CDCl$_3$) δ 1.95-2.10 (m, 2H), 2.55-2.2.70 (m, 2H), 3.85 (s, 6H), 4.60-4.65 (m, 1H), 6.65-6.80 (m, 4H), 6.85 (s, 2H), 7.15-7.19 (m, 1H).

Example 2

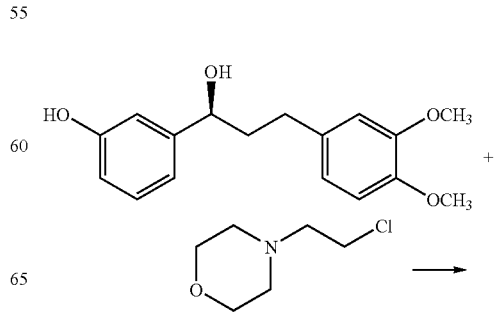

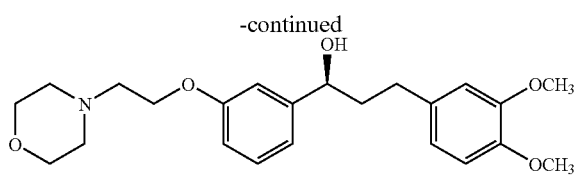

The compound prepared in Example 1, (3-((S)-1-hydroxy-3-(3,4-dimethoxyphenyl)propyl)phenol, 1.0 g, 3.46 mmol), 4-(2-chloroethyl)morpholine (1.3 g, 6.9 mmol), and potassium carbonate (2.0 g, 13.8 mmol) were added to DMF (10.0 mL). The mixture was heated to 60° C. and stirred for 48 h at this temperature. The reaction was cooled to rt, water was added and the mixture was then extracted with DCM. The organic layer was separated, washed with solution of 1 N HCl (4×), water (2×), and brine. The combined organic extract was dried over anhy MgSO$_4$, and evaporation of solvent afforded the product ((S)-1-(3-(2-morpholinoethoxy)phenyl)-3-(3,4-dimethoxyphenyl)propan-1-ol) as yellow oil (1.2 g, 85% yield).

$^1$H NMR (500 MHz, CDCl$_3$) δ 1.95-2.10 (m, 2H), 2.55-2.85 (m, 8H), 3.70-3.85 (m, 4H), 4.85 (s, 6H), 4.10-4.15 (m, 2H), 4.60-4.65 (m, 1H), 6.70-6.80 (m, 4H), 6.85-6.90 (m, 2H), 7.15-7.19 (m, 1H).

Example 3

Preparation of (S)-1-(4-(2-Morpholinoethoxyphenyl)-3-(3,4-dimethoxyphenyl)propyl Methanesulfonate

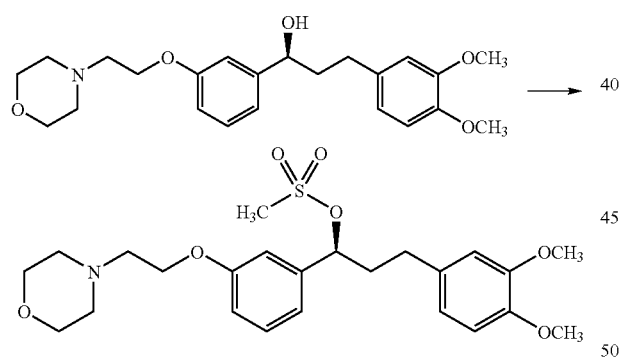

To a solution of (S)-1-(3-(2-morpholinoethoxyphenyl)-3-(3,4-dimethoxyphenyl)propan-1-ol (0.4 g, 1.0 mmol) in dichloromethane (5.0 mL) under N$_2$ was added triethylamine (0.4 g, 4.0 mmol). The solution was then cooled to 0° C., methanesulfonyl chloride (0.28 g, 2.5 mmol) was added, and the reaction was stirred at 0° C. for 1.5 h. Ice cold water (5.0 mL) was added to the reaction mixture and it was extracted with dichloromethane. The combined organic extract was washed with a cold solution of ammonium chloride, brine, then dried over anhydrous MgSO$_4$. Evaporation of the solvent afforded (S)-1-(3-(2-morpholinoethoxyphenyl)-3-(3,4-dimethoxyphenyl)propyl methanesulfonate (0.42 g, 88% yield).

$^1$H NMR (500 MHz, CDCl$_3$) δ 1.95-2.08 (m, 1H), 2.25-2.32 (m, 1H), 2.50-2.65 (m, 4H), 2.80-3.15 (m, 4H), 3.70-3.75 (m, 6H), 3.78-3.9 (br s, 4H), 4.2-4.3 (br s, 2H), 4.60-4.65 (m, 1H), 6.60-6.65 (m, 2H), 6.68-6.75 (m, 1H), 6.80-6.95 (m, 2H), 7.20-7.30 (m, 2H).

Example 4

Preparation of 4-(2-(4-((R)-1-Azido-3-(3,4-dimethoxyphenyl)propylphenoxy)ethyl)morpholine

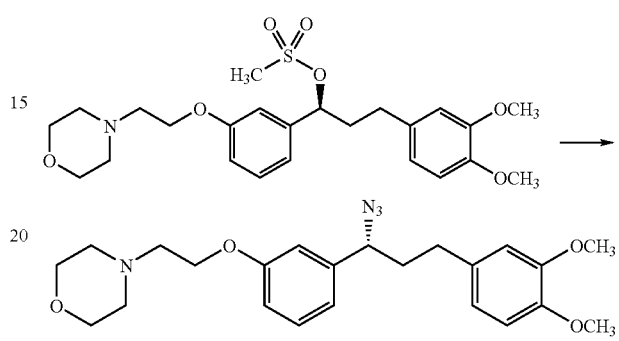

(S)-1-(3-(2-Morpholinoethoxyphenyl)-3-(3,4-dimethoxyphenyl)propyl methanesulfonate (0.42 g, 0.9 mmol) was dissolved in DMF (8.0 mL), sodium azide (0.2 g, 3.6 mmol) was added, and the mixture was stirred at rt for 48 h. Water (20 mL) was added, and the mixture was extracted with ethyl acetate. The organic layer was dried over MgSO$_4$, the solids were removed by filtration, and evaporation of solvent under vacuum afforded 3-(2-(4-((R)-1-azido-3-(3,4-dimethoxyphenyl)propylphenoxy)ethyl)morpholine as yellow oil (0.4 g, quantitative yield). The crude product was used directly without further purification directly in the next reduction step as shown in Example 5.

Example 5

Preparation of (R)-1-(4-(2-Morpholinoethoxy)phenyl)-3-(3,4-dimethoxylphenyl)propan-1-amine

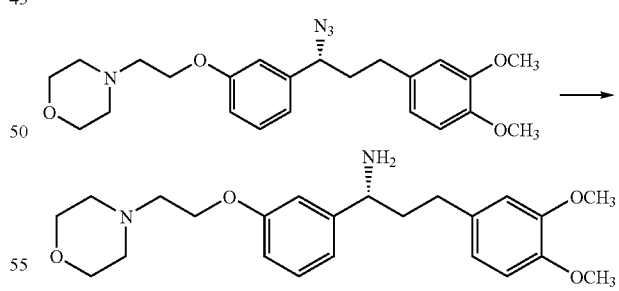

2-(4-((R)-1-Azido-3-(3,4-dimethoxyphenyl)propylphenoxy)ethyl)morpholine (Example 4, 0.4 g, 0.9 mmol) was dissolved in methanol (4.0 mL), pyridine (0.1 g, 1.1 mmol) and Pd(OH)$_2$ (0.02 g, catalytic amount) were added and the reaction mixture was flushed with H$_2$ (balloon) at rt. The reaction was stirred under H$_2$ for 48 h. The catalyst was removed by pad of Celite®, and evaporation of the solvent afforded light brown oil. The oil was dissolved in dichloromethane (15 mL), and washed successively with HCl (1 N), NaOH (1 N), water and brine. The organic layer was dried over MgSO₄, the solids were removed by filtration. Evaporation of the solvent afforded the product (R)-1-(3-(2-morpholinoethoxy)phenyl)-3-(3,4-dimethoxyphenyl)propan-1-amine (0.35, 93% yield).

¹H NMR (500 MHz, CD₂Cl₂) δ 1.80-1.88 (m, 2H), 2.32-2.55 (m, 6H), 2.62-2.70 (m, 2H), 3.55-3.60 (m, 4H), 3.70 (s, 7H), 3.95-4.05 (m, 2H), 6.58-6.65 (m, 2H), 6.68-6.72 (m, 2H), 6.78-6.85 (m, 2H), 7.12-7.20 (m, 1H).

Example 6

Preparation of (2S)-1-((S)-2-(3,4,5-Trimethoxyphenyl)butanoyl)-N—((R)-1-(4-(2-morpholinoethoxy)phenyl)-3-(3,4-dimethoxyphenyl)propyl)piperidine-2-carboxamide

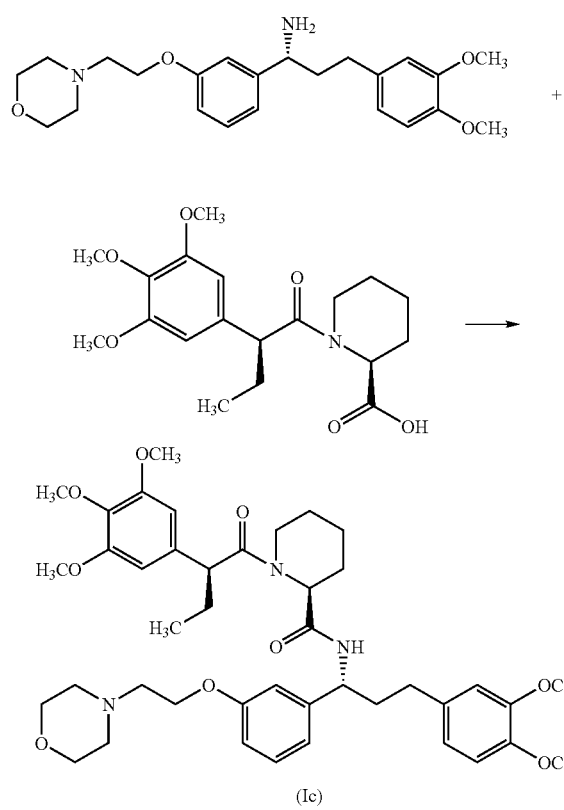

R)-1-(3-(2-Morpholinoethoxy)phenyl)-3-(3,4-dimethoxyphenyl)propan-1-amine (0.05 g, 0.12 mmol) and 1-((S)-2-(3,4,5-trimethoxyphenyl)butanoylpiperidine-2-carboxylic acid (0.05 g, 0.14 mmol) were dissolved in dichloromethane (4.0 mL). DCC (0.037 g, 0.18 mmol) and DMAP (3.0 mg, 0.03 mmol) were added, and the reaction was stirred at rt for 24 h. The solvent was the removed and the product was purified by preparative TLC eluting with 2% methanol/ethyl acetate affording 40 mg (55% yields) of (2S)-1-((S)-2-(3,4,5-trimethoxyphenyl)butanoyl)-N—((R)-1-(4-(2-morpholinoethoxy)phenyl)-3-(3,4-dimethoxyphenyl)propyl)piperidine-2-carboxamide (Ic) as white solid.

(¹H NMR (500 MHz, CD₂Cl₂) δ 1.80-1.88 (m, 2H), 2.32-2.55 (m, 6H), 2.62-2.70 (m, 2H), 3.55-3.60 (m, 4H), 3.70 (s, 7H), 3.95-4.05 (m, 2H), 6.58-6.65 (m, 2H), 6.68-6.72 (m, 2H), 6.78-6.85 (m, 2H), 7.12-7.20 (m, 1H).

Example 7

Preparation of (S)-Methyl 1-(N-ethyl-N-phenylcarbamoyl)piperidine-2-carboxylate

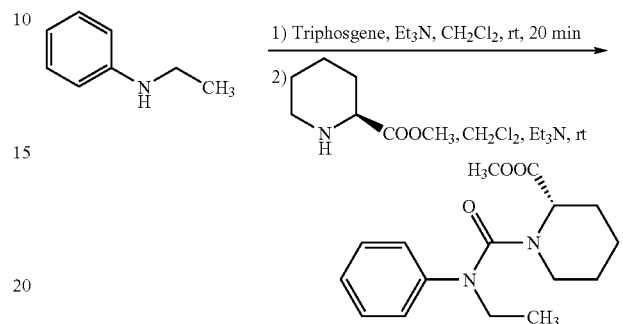

N-Ethylbenzeneamine (0.12 g, 1.0 mmol) was dissolved in dichloromethane (5.0 mL), and triethylamine (0.2 g, 2.0 mmol) was added, followed by the addition of triphosgene (0.12 g, 0.4 mmol) in dichloromethane (2.0 mL). The reaction was stirred at rt for 20 min, then a solution of S-methyl piperidine-2-carboxylate and triethylamine (0.4 g, 4.0 mmol) were added in dichloromethane (4.0 mL). The reaction was stirred at rt for 72 h. The solvent was removed and purification was accomplished by silica gel chromatography (50% ethyl acetate/hexanes to ethyl acetate) and the product-containing fractions were combined to afford (S)-methyl 1-(N-ethyl-N-phenylcarbamoyl)piperidine-2-carboxylate (65% yield). ¹H NMR (500 MHz, CD₂Cl₂) 61.00-1.10 (t, 3H), 1.15-1.30 (m, 4H), 1.42-1.50 (m, 2H), 1.80-1.85 (d, 1H), 2.65-2.80 (m, 1H), 3.50-3.55 (m, 1H), 3.6 (s, 3H), 3.65-3.70 (m, 1H), 4.6 (t, 1H), 7.00-7.10 (m, 2H), 7.12-7.7.15 (m, 1H), 7.20-7.25 (m, 1H), 7.30-7.40 (m, 1H).

Example 8

Preparation of (S)-1-(N-Ethyl-N-phenylcarbamoyl)piperidine-2-carboxylic Acid

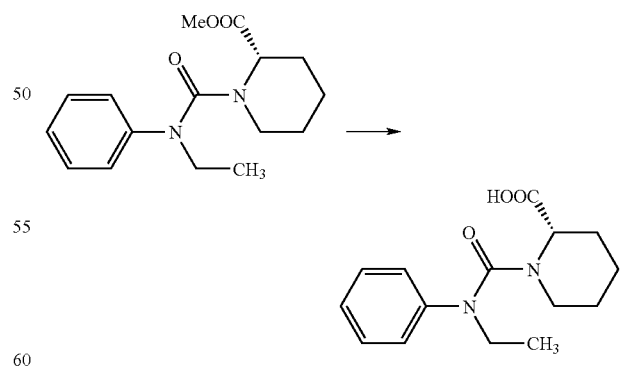

To (S)-methyl 1-(N-ethyl-N-phenylcarbamoyl)piperidine-2-carboxylate (0.15 g, 0.5 mmol) dissolved in methanol (2.0 mL) was added a solution of LiOH (1.0 N, 8.0 equiv). The reaction was heated to 50° C. and stirred at this temperature for 4 h. The solvent was then removed and pH was adjusted to 4 by addition of 1N HCl. The mixture was extracted with dichloromethane and evaporation of the solvent afforded (S)-1-(N-ethyl-N-phenylcarbamoyl)piperidine-2-carboxylic acid (0.1 g, 72% yield). $^1$H NMR (500 MHz, $CD_2Cl_2$) δ 1.00-1.10 (m, 4H), 1.40-1.55 (m, 3H), 2.10 (m, 2H), 2.5 (m, 1H), 3.2 (d, 1H), 3.50-3.55 (m, 2H), 3.65-3.70 (m, 1H), 4.4 (t, 1H), 7.10-7.25 (m, 3H), 7.30-7.45 (m, 2H), 12.5 (br s, 1H).

Example 9

Preparation of (2S)—$N^2$—((R)-1-(4-2-morpholinoethoxy)phenyl)-3-(3,4-dimethoxyphenyl)propyl)-$N^1$-ethyl-$N^1$-phenylpiperidine-1,2-dicarboxamide

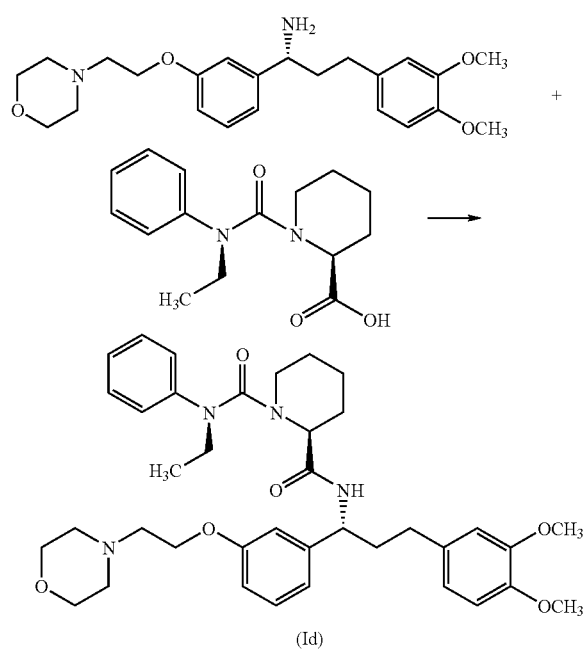

(Id)

(R)-1-(3-(2-Morpholinoethoxy)phenyl)-3-(3,4-dimethoxylphenyl)propan-1-amine (0.05 g, 0.12 mmol) and (S)-1-(N-ethyl-N-phenylcarbamoyl)piperidine-2-carboxylic acid (0.04 g, 0.14 mmol) were dissolved in dichloromethane (4.0 mL). DCC (0.037 g, 0.18 mmol), and DMAP (3.0 mg, 0.03 mmol) were added and the reaction was stirred at rt for 24 h. The solvent was the removed and the product was purified by preparative TLC eluting with 2% methanol/ethyl acetate affording 44 mg (54% yields) of (2S)-M-((R)-1-(3-2-morpholinoethoxy)phenyl)-3-(3,4-dimethoxyphenyl)propyl)-$N^1$-ethyl-$N^1$-phenylpiperidine-1,2-dicarboxamide (Id) as white solid. $^1$H NMR (500 MHz, $CD_2Cl_2$) δ 1.00-1.10 (m, 6H), 1.25-1.40 (m, 2H), 1.85-2.10 (m, 3H), 2.40-2.55 (m, 5H), 2.60-2.65 (m, 2H), 3.30 (d, 1H), 3.35-3.38 (q, 2H), 3.55-3.65 (m, 3H), 3.70-3.75 (m, 3H), 3.95-4.10 (m, 2H), 4.5 (br s, 1H), 4.72-4.80 (m, 1H), 6.58-6.80 (m, 5H), 7.05-7.20 (m, 4H), 7.25-7.30 (m, 2H), 7.60-7.65 (m, 1H).

Example 10

Bioassay Evaluation

The compounds were assayed for their ability to bind to the destabilizing domain of the protein according the following procedure:

HCT116 cells stably transfected with L106-tsLuc were cultured in DMEM media containing 10% fetal bovine serum. 7,000 cells/well were seeded in 100 μL of DMEM/10% FBS media in a 96-well plate and incubated overnight at 37° C. in a humidified, 5% $CO_2$ incubator. Media was replaced with fresh 100 μL of fresh DMEM/10% FBS media containing various concentrations of Shield-1, and the compounds of Example 6 (Ic), and Example 9 (Id) Compounds were added at 3-fold dilutions, concentrations ranging from 10 μM to 12 nM. After 24 hour incubation with the compounds at 37° C. in a humidified, 5% $CO_2$ incubator, luciferase activity was measured in a luminometer after the addition of 100 μL/well BrightGlo reagent (Promega).

In this experiment, the tested compounds exhibited the following luciferase activity, expressed in $IC_{50}$ values as follows:

| | |
|---|---|
| Shield-1 | <10 nM |
| Example 6 (Ic) | <100 nM |
| Example 9 (Id) | <10 μM |

Equivalents

Although particular embodiments have been disclosed herein in detail, this has been done by way of example for purposes of illustration only, and is not intended to be limiting with respect to the precise form of the disclosed invention or to the scope of the appended claims that follow. In particular, it is contemplated by the inventors that various substitutions, alterations, and modifications may be made to the invention without departing from the spirit and scope of the invention as defined by the claims. Various alterations and modifications of the invention are believed to be a matter of routine for a person of ordinary skill in the art with knowledge of the embodiments described herein. Other aspects, advantages, and modifications considered to be within the scope of the following claims.

What is claimed is:

1. A compound of formula (I)

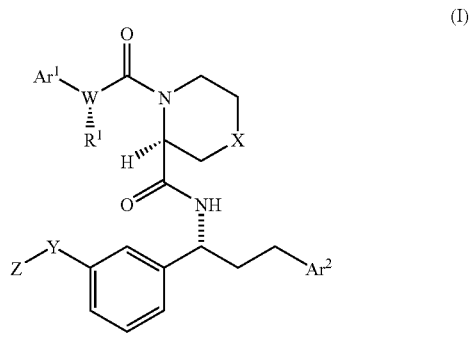

wherein

W is CH or N;

$R^1$ is ($C_1$-$C_6$)alkyl;

Y is O, $CH_2$, S, NH, or $NR^2$;

$R^2$ is ($C_1$-$C_6$)alkyl;

X is $CH_2$, O, NH, N(($C_1$-$C_6$)alkyl);

Z is selected from

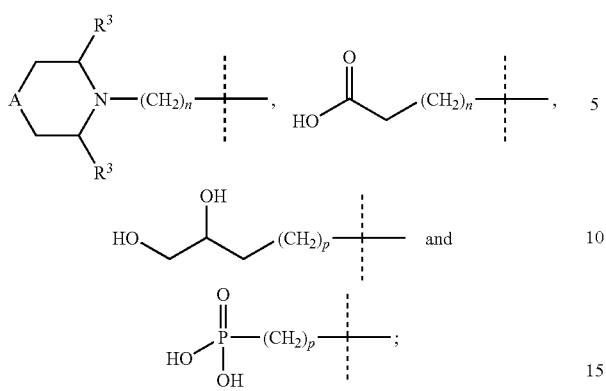

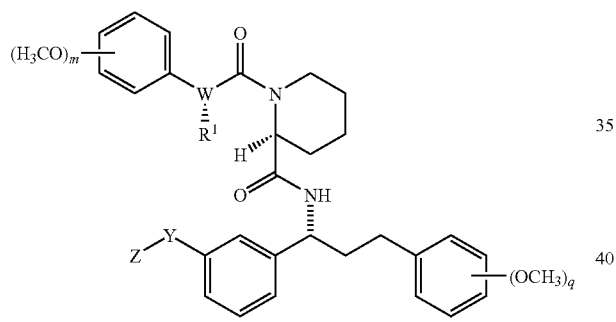

wherein
A is O, CH$_2$, S, NH, or NR$^2$;
R$^3$ is (C$_1$-C$_6$)alkyl;
n is 1, 2, 3, 4 or 5;
p is 0, 1, 2, 3, 4 or 5;
Ar$^1$ and Ar$^2$ are each independently phenyl, optionally substituted by 1-3 groups selected from (C$_1$-C$_3$)alkyl, (C$_1$-C$_3$)alkoxy, and halo;
and the pharmaceutically acceptable salts thereof.

2. The compound of Formula (Ia)

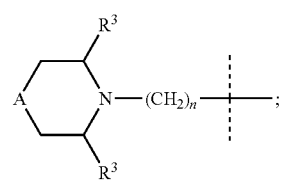

(Ia)

wherein
W is C or N;
R$^1$ is (C$_1$-C$_6$)alkyl;
Y is O, CH$_2$, S, NH, or NR$^2$;
m is 0, 1, 2 or 3;
q is 0, 1 or 2;
Z is wherein
n is 2, 3, 4 or 5;
A is O, CH$_2$, S, NH, or NR$^2$;
R$^2$ and R$^3$ are independently (C$_1$-C$_6$)alkyl;
and the pharmaceutically acceptable salts thereof.

3. A compound selected from
(2S)—N$^2$—((R)-1-(4-2-morpholinoethoxy)phenyl)-3-(3,4-dimethoxyphenyl)propyl)-N$^1$-ethyl-N$^1$-phenylpiperidine-1,2-dicarboxamide; and
(2S)-1-((S)-2-(3,4,5-trimethoxyphenyl)butanoyl)-N—((R)-1-(4-(2-morpholinoethoxy)phenyl)-3-(3,4-dimethoxyphenyl)propyl)piperidine-2-carboxamide.

* * * * *